United States Patent [19]

Olesen

[11] 4,434,790

[45] Mar. 6, 1984

[54] VAPORIZER SUBSYSTEM FOR AN ANESTHESIA MACHINE

[75] Inventor: Russell Olesen, Huntington, N.Y.

[73] Assignee: Puritan-Bennett Corporation, Kansas City, Mo.

[21] Appl. No.: 293,994

[22] Filed: Aug. 18, 1981

[51] Int. Cl.³ ............................................. A61M 11/00
[52] U.S. Cl. ............................ 128/200.14; 128/200.19; 137/637.1; 137/614.06; 74/483 K
[58] Field of Search ...................... 128/200.14, 200.19, 128/203.12; 137/637.1, 614.06; 74/483 K, 483 R

[56] References Cited

U.S. PATENT DOCUMENTS

| | | | |
|---|---|---|---|
| 2,692,617 | 10/1954 | Jensen | 137/637.1 |
| 4,246,115 | 1/1981 | Swank | 74/483 K |
| 4,346,701 | 8/1982 | Richards | 128/200.19 |

FOREIGN PATENT DOCUMENTS

| | | | |
|---|---|---|---|
| 468379 | 4/1914 | France | 74/483 R |
| 2077042 | 12/1981 | United Kingdom | 74/483 R |

*Primary Examiner*—Henry J. Recla
*Attorney, Agent, or Firm*—Fulwider, Patton, Rieber, Lee & Utecht

[57] ABSTRACT

An assembly of isolation valves (42, 44, 46) coupled to vaporizers (54, 56, 69), and a corresponding number of valve control levers (66, 68, 70) connected by an interlock mechanism that allows only one of the levers to be in an on position at any time. The interlock mechanism includes a cable (80, 81, 82) between each unique pair of control levers, the cables being only long enough to permit one lever of each unique pair to be moved to the on position. Each lever has a camming roller (66d, 68d, 70d) that engages and rotates a forked valve cam (86) to switch the valve on or off.

11 Claims, 9 Drawing Figures

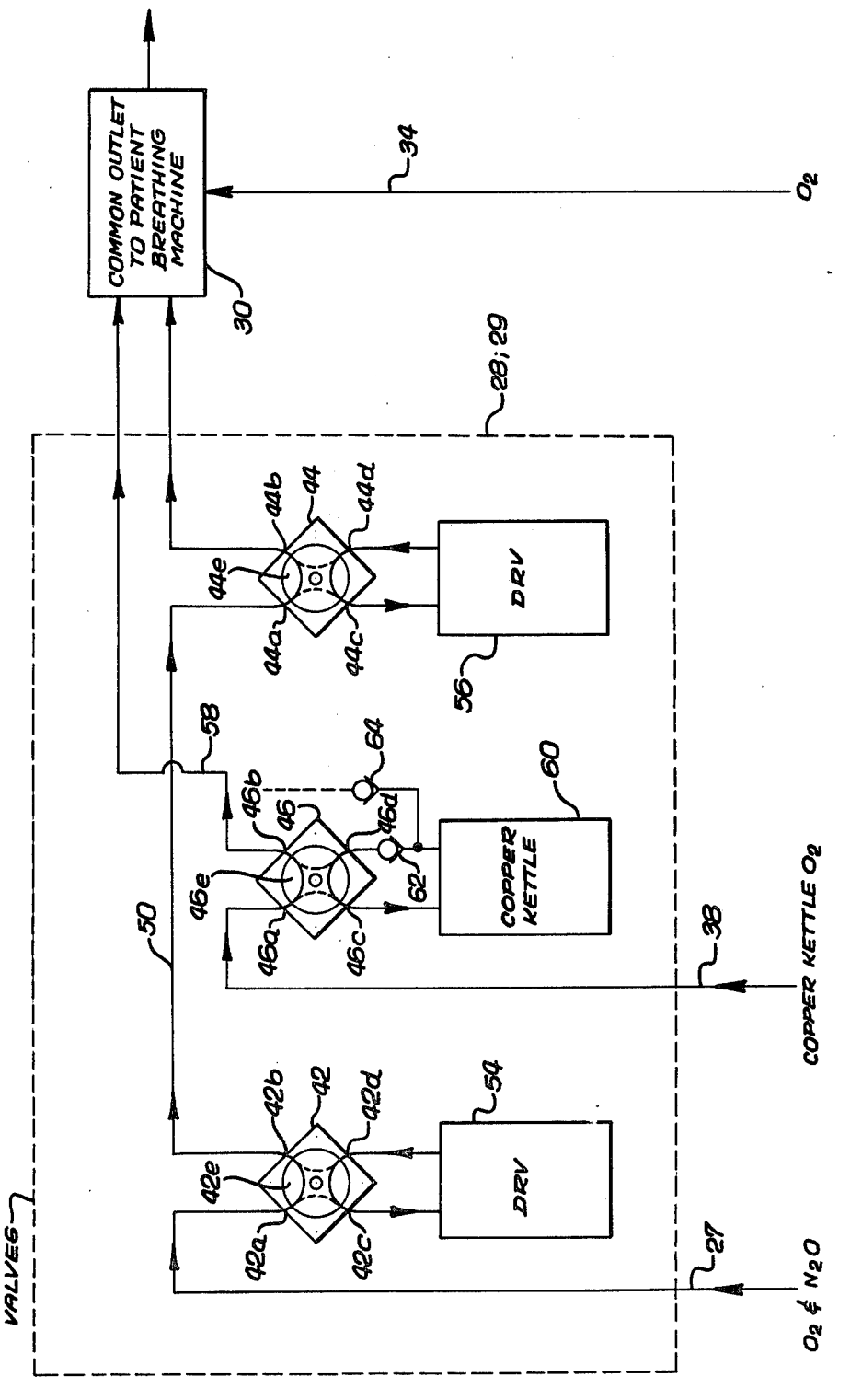

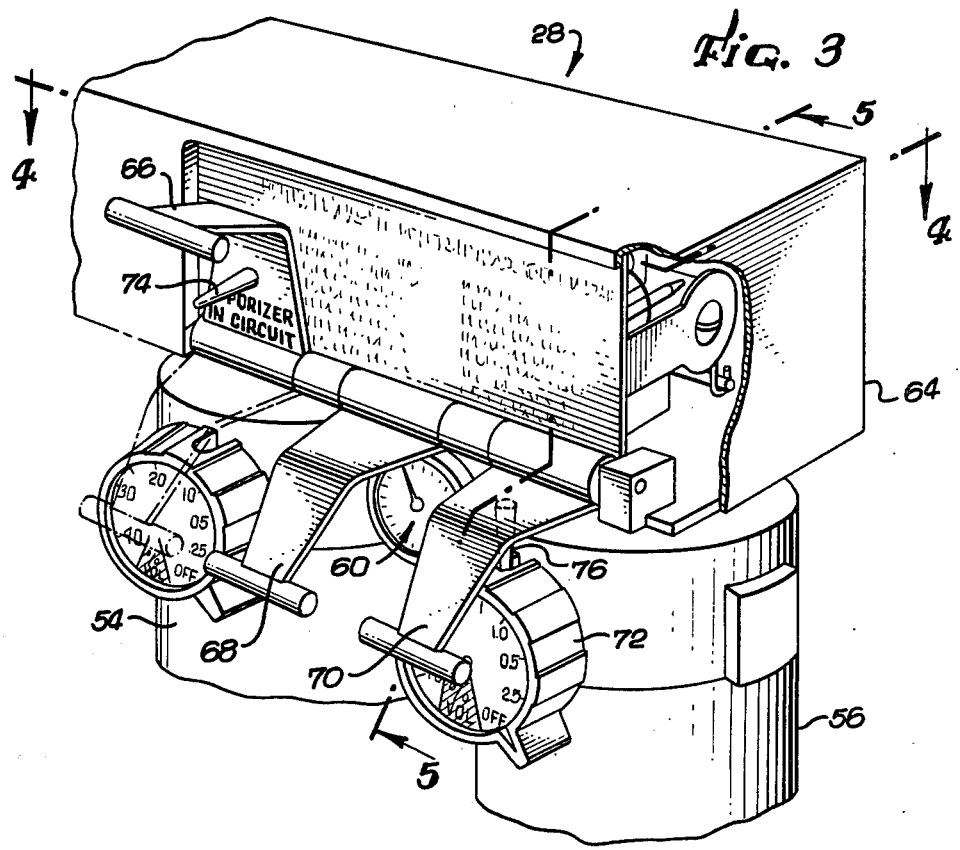
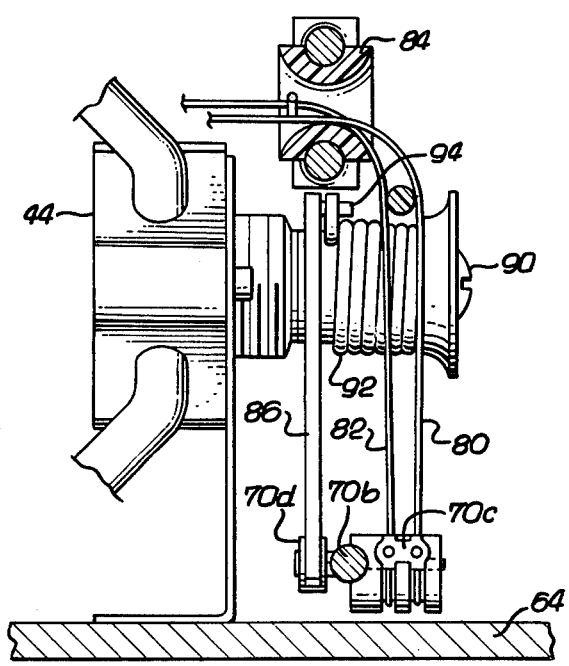

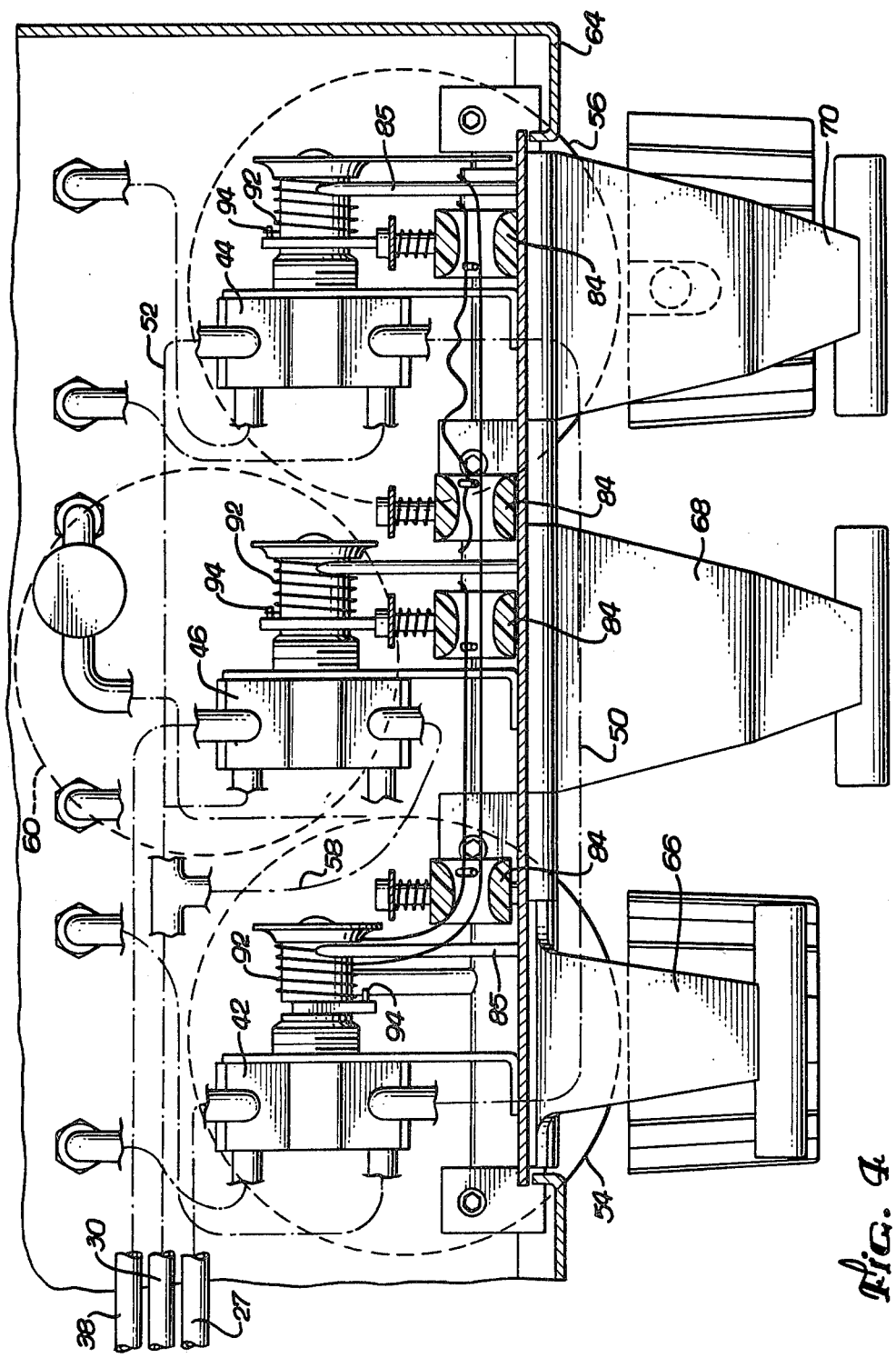

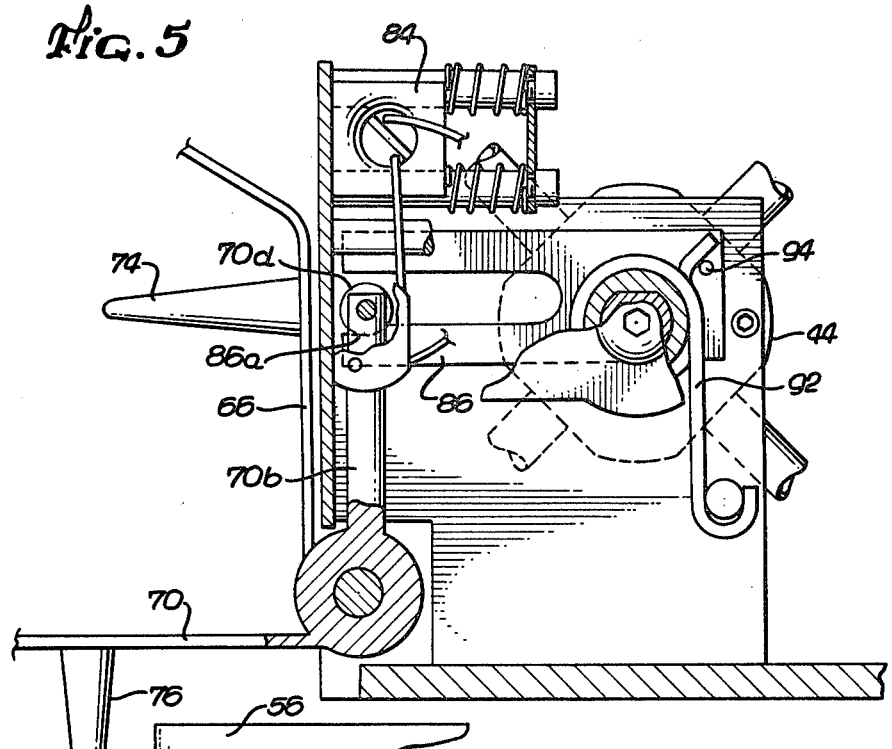
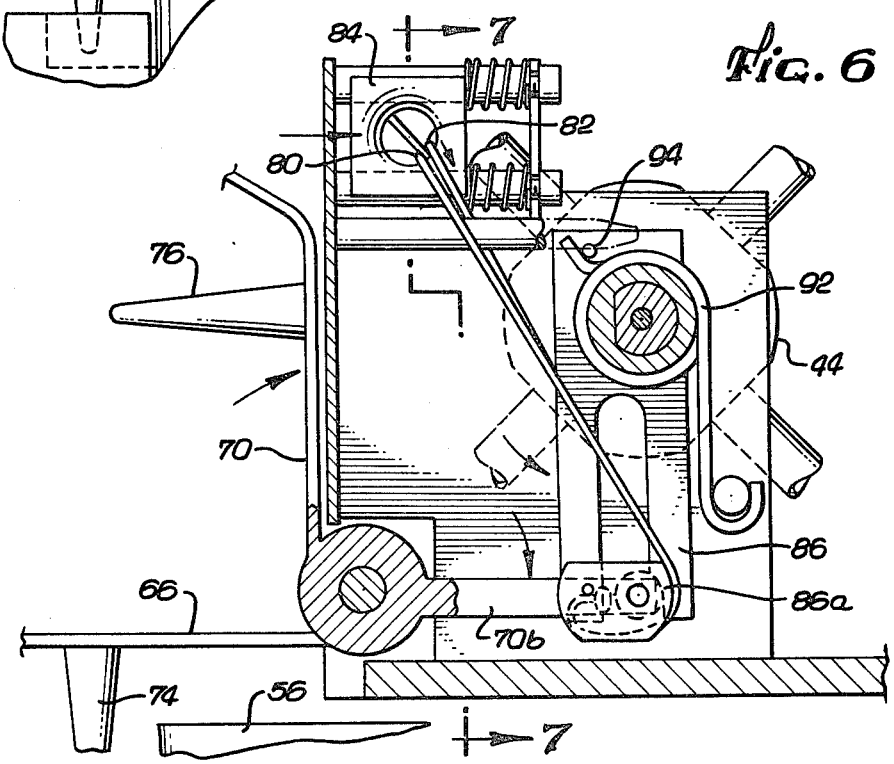

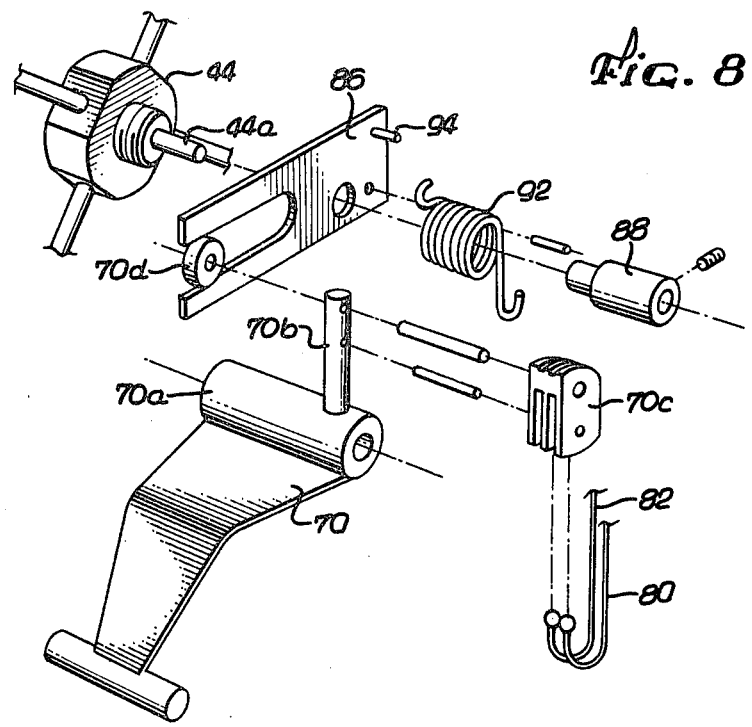
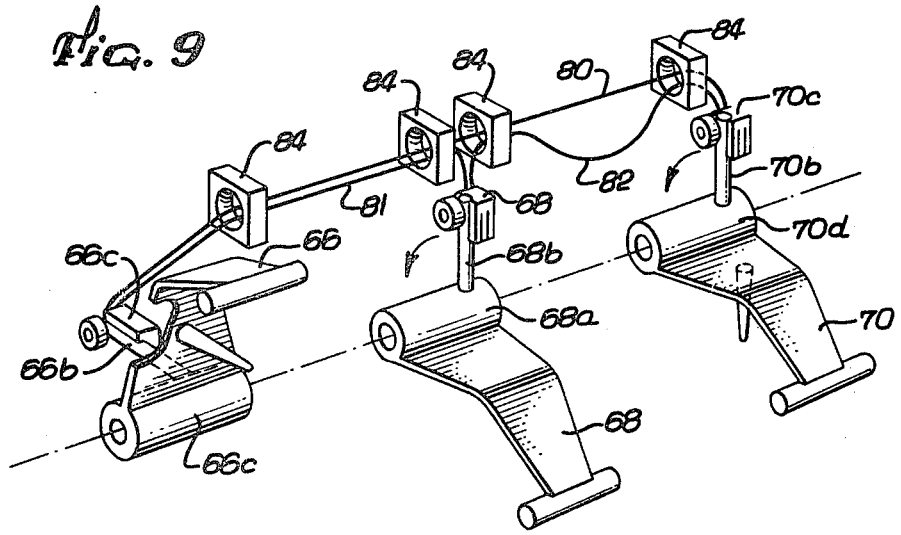

VAPORIZER SUBSYSTEM FOR AN ANESTHESIA MACHINE

BACKGROUND OF THE INVENTION

This invention relates generally to gas anesthesia machines, and, more particularly, to subsystems in such machines for adding vapors to a mixture of anesthesia gas and oxygen.

A gas anesthesia machine includes an oxygen supply, a supply of anesthesia gas, such as a nitrous oxide ($N_2O$), flow control valves and flow meters for the anesthesia gas and the oxygen, and a common outlet by means of which a mixture of the gases is passed to a patient breathing machine. The patient breathing machine, which forms no part of the present invention, is typically a closed-circuit system including a carbon dioxide absorber and at least two check valves, to ensure that the patient inhales gas from the common outlet and exhales through the carbon dioxide absorber. The patient breathing machine may also include a ventilator to pump breathing gas into the patient's lungs, and a gas evacuation system for removal of excess gas. In simple terms, a gas anesthesia machine provides a mixture of anesthesia gas and oxygen in proportions selected by an operator, who is usually a doctor.

On many occasions, the doctor or anesthesiologist wishes to add another substance in vapor form to the mixture of anesthesia gas and oxygen. For this purpose, the gases are passed through a vaporizer from which the added substance is removed, usually by evaporation, before passing to the common outlet and thence to the patient breathing machine.

There are a number of different specific types of vaporizers, but only two general types with which this invention is concerned. First there are direct reading vaporizers. As the name implies, a direct reading vaporizer has a control knob graduated in terms of the percentage concentration of the vapor that is added to a gas stream passing through the vaporizer. A direct reading vaporizer is inserted into the oxygen and anesthesia gas flow immediately prior to the common outlet, to allow the addition of a selected concentration of vapor to the combined gases. The other type of vaporizer with which the invention is concerned is the universal vaporizer, sometimes referred to as a copper kettle vaporizer. The universal vaporizer adds vapor to an independently controlled oxygen circuit, i.e., a separate circuit comprising a flow control valve and flow meter. The universal vaporizer flow can be calibrated in advance and can be used independently of the main oxygen and anesthesia gas flow. Depending on the requirements for a particular surgical procedure, the doctor may have need for one or more direct reading vaporizers at various times, as well as for a universal vaporizer. Accordingly, there is a need to provide for convenient switching from one vaporizer to another, while ensuring at all times that only one vaporizer is connected to the patient breathing machine any particular time.

Some systems utilize the off position of direct reading vaporizers to ensure that only one vaporizer is not connected at any particular time. Although this should theoretically isolates unused vaporizers from the rest of the system, there is always the possibility of a malfunction of the vaporizer controls, so that a vaporizer in the off position could still add vapor to the diluent stream of gases from the gas anesthesia machine. Ideally, then, the unused vaporizers should be completely isolated from the diluent flow, even when a faulty control leaks in the off position. One prior art technique of providing such isolation is to mount the vaporizers in a rotatable turret so constructed that only one vaporizer at a time can be connected into the diluent flow. Such a system utilizes quick disconnect devices to disconnect one vaporizer and reconnect another after rotating the turret to the appropriate position. Although such a system provides isolation and inherently prevents the use of more than one vaporizer, the system is relatively inconvenient to use and still relies on the off position of the control knob for the vaporizer that is connected to the system. Thus, the isolation provided by a turret system is not reliably complete, since a malfunction of the connected vaporizer could still add vapor to the diluent flow.

It will be apparent from the foregoing discussion that there are basically three requirements for an ideal vaporizer subsystem. First, there should be isolation of all unused vaporizers, even when all vaporizers are unused. Second, there should be a convenient and reliable interlock device to ensure that only one vaporizer may be selected at any time, whether the selected vaporizer is a direct reading vaporizer or a vaporizer of the universal type. Finally, there should be a clear visual indication, preferably visible from some distance, of which vaporizer is connected to the diluent flow. The present invention is directed to a vaporizer subsystem that satisfies these three ideal requirements and overcomes the disadvantages of prior subsystems of this type.

SUMMARY OF THE INVENTION

The present invention resides in a vaporizer subsystem for use with a gas anesthesia machine, the subsystem providing means for selecting one of a plurality of vaporizers, which may be direct reading vaporizers or of the universal type, while at the same time isolating non-selected vaporizers and providing a visual indication of which vaporizer is connected to the diluent flow. Basically, and in general terms, the vaporizer subsystem of the invention includes a plurality of isolation valve control levers and an equal plurality of isolation valves, one for each vaporizer that can be connected to the system, each isolation valve having an on position in which the corresponding vaporizer is connected in series with the diluent flow and an off position in which the vaporizer is isolated from the diluent flow.

The plurality of valve control levers are interconnected by mechanical interlock means so arranged that only a selected one of the levers may be placed in the on position at any time. Furthermore, a control lever in the off position covers the upper portions of a vaporizer not selected for use, and a control lever in the on position uncovers its vaporizer and provides a clear indication that the vaporizer has been selected for use. As a further precaution, control knobs on the non-selected direct reading vaporizers must also be in the off position before the control levers can be moved fully to the off position. Thus, no vaporizer can be selected until all of the non-selected direct reading vaporizers are turned to the off position.

More specifically, the vaporizers are arrayed in a row, and the control levers are disposed likewise in a row above the vaporizers. The interlock means includes a plurality of cables there being a cable running from each lever to each of the other levers. Thus, if there are N levers there are $N(N-1)/2$ cables. In particular, if there are three levers there are three cables, four levers six cables and so forth. When all the levers are in the off position, all the cables have a slack length equivalent to the full movement of a lever. Thus, if one lever is raised to the on position all of the cables to which it is attached will be fully tightened, and no other lever can be raised without first lowering the lever that is already raised.

The levers operate the isolation valves by means of a Geneva mechanism, and the valves are biased toward the off position by means of torsion springs. When a lever is moved to the on position, the spring will hold the lever there in a detent, but will return it to the off position if the lever is moved slightly away from the on position. This can be accomplished by raising one of the non-selected levers, thus pulling on the already tight cable between the newly selected lever and the one already in the on position. The spring coupled to the first selected lever will then return it to the off position and the newly selected lever may be raised to the on position. In no event, however, can any lever be raised fully to the on position unless all the non-selected levers are in the fully off position.

It will be appreciated from the foregoing that the present invention provides a significant advance in the field of gas anesthesia machines. In particular, it provides a vaporizer subsystem in which only one vaporizer may be selected while the non-selected vaporizers are simultaneously isolated and a clear visual indication is given of which vaporizer has been selected and turned on. Other aspects and advantages of the present invention will become apparent from the following more detailed description, taken in junction with the accompanying drawings.

BRIEF DESCRIPTION OF THE DRAWINGS

FIG. 2 is a schematic or circuit diagram of the vaporizer subsystem of the invention, showing flow paths through isolation valves;

FIG. 3 is a perspective view of the vaporizer subsystem of the invention;

FIG. 4 is an enlarged plan view of the vaporizer subsystem, partly in section and taken substantially along the line 4—4 in FIG. 3;

FIG. 5 is a sectional view taken substantially along the line 5—5 in FIG. 3, and showing a first valve in the off position;

FIG. 6 is a sectional view similar to FIG. 5 but showing the first valve in the on position;

FIG. 7 is a sectional view taken substantially along the line 7—7 in FIG. 6;

FIG. 8 is an exploded perspective view of an isolation valve and control lever assembly; and FIG. 9 is a fragmentary perspective view illustrating operation of the cable interlock mechanism.

DESCRIPTION OF THE PREFERRED EMBODIMENT

Figure 1:
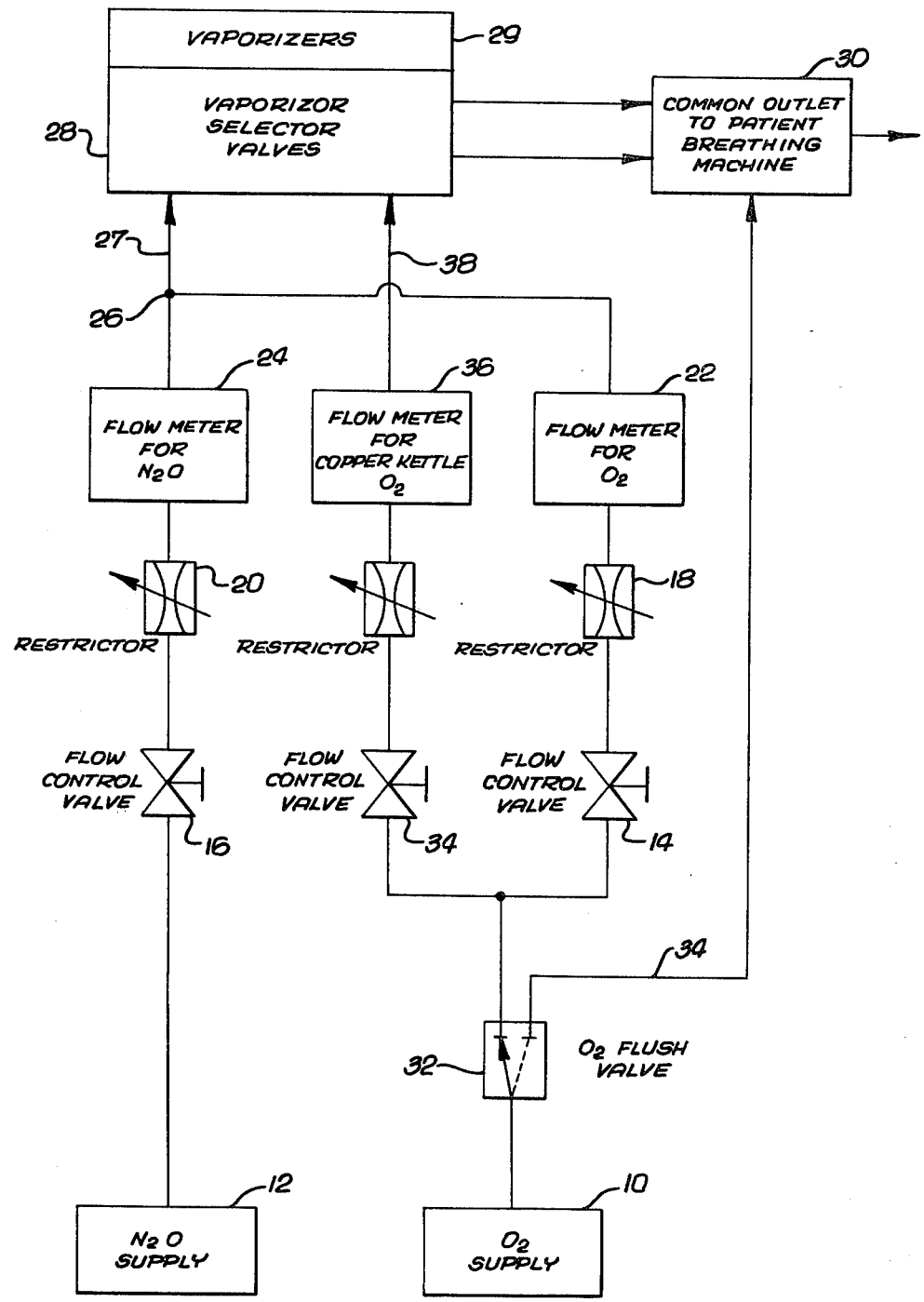
FIG. 1 is a simplified schematic diagram of a gas anesthesia machine in conjunction with which the present invention is employed.

As shown in the drawings for purposes of illustration, the present invention is principally concerned with a vaporizer subsystem for use in a gas anesthesia machine. FIG. 1 shows the basic configuration of a gas anesthesia machine including an oxygen supply, indicated generally by reference numeral 10, a nitrous oxide supply 12, oxygen and nitrous oxide flow control valves 14 and 16, respectively, oxygen and nitrous oxide flow restrictors 18 and 20 respectively, and oxygen and nitrous oxide flow meters 22 and 24, respectively. The gas supplies 10 and 12 are connected through the respective flow control valves 14 and 16, thence through the respective restrictors 18 and 20 and through the respective flow meters 22 and 24. The gas flow from the flow meters 22 and 24 is then combined at a single manifold, as indicated at 26, and passed over line 27 to vaporizer selector valves, indicated generally at 28, for connection to vaporizers 29 on a selected basis, and thence to a common outlet indicated at 30. The common outlet is connected to a patient breathing machine (not shown) which typically includes a carbon dioxide absorber and check valves to ensure that the patient inhales only from the common outlet and exhales only into the carbon dioxide absorber. The patient breathing machine may also include a ventilator to pump the nitrous oxide and oxygen into the patient's lungs, and a gas evacuation system for removing excess anesthesia gas from the patient breathing machine.

Also shown in FIG. 1 is an oxygen flush valve 32 connected in the oxygen supply line between the supply 10 and the control valve 14. The purpose of the flush valve 32 is to provide a means for diverting the oxygen flow, as shown by line 34, directly to the common outlet 30, for use in situations in which a pure oxygen flow is needed to flush the patient breathing machine. For use in conjunction with a universal vaporizer, there is also an additional oxygen flow control valve 34, and an additional flow meter 36. Oxygen for this flow path is derived from the common oxygen supply 10, and passed first through the flow control valve 34, then through the flow meter 36 and over line 38 to the vaporizer selector valves 28.

In accordance with the invention, and as shown in FIG. 2, the diluent flow on line 27 passes through a number of isolation valves, shown by way of example as the two valves 42 and 44, before merging at the common outlet 30. The independent oxygen flow on line 38 is coupled to a similar isolation valve 46 before merging at the common outlet 30. The vaporizer subsystem of the invention operates in such a manner that only one of the vaporizer isolation valves 42, 44 or 46 can be operative to divert the flow therethrough at any time.

It will be noted that each of the valves 42, 44 and 46 has four ports, indicated by the suffixes a, b, c and d, respectively, appended to the reference numerals by which the isolation valves are indicated. Line 27 is coupled to port 42a and port 42b is connected by line 50 to port 44a of the next isolation valve. Port 44b is connected by line 52 to the common outlet 30. Ports 42c and 42d are coupled to a direct reading vaporizer 54 and ports 44c and 44b are coupled to another direct reading vaporizer 56. Line 38 from the independent oxygen supply is coupled to port 46a, and port 46b is coupled to line 58 to the common outlet 30. Port 46c is coupled to a universal vaporizer 60, which is also coupled to port 46d through a check valve 62. Check valve 62 typically incorporates a pressure relief valve 64 as well.

It will be noted that each of the isolation valves 42, 44 and 46 includes a central rotatable portion indicated by suffix e. Each of these rotatable portions 42e, 44e and 46e has a pair of passages for placing two adjacent ports in communication. When the valves are in the off position, ports with the reference numeral suffixes a and b are in fluid communication, as well as ports with the suffixes c and d. When a valve is in the on position, however, ports a and c are in fluid communication and ports b and d are in fluid communication. Thus, as illustrated by the solid lines in the isolation valves shown in FIG. 2, when the valves are off line 27 communicates directly with line 50, which communicates directly with line 52 and thence to the common outlet 30. Similarly, line 38 communicates directly with line 58 to the common outlet 30. If, for example, isolation valve 42 is switched to the on position, the flow of gas is from line 27 through ports 42a and 42c to the vaporizer 54, and thence back through ports 42d and 42b to line 50. It will be apparent that the isolation valves 42, 44 and 46 are effective to completely isolate non-selected vaporizer units. Even if none of the vaporizers is selected for use, all are completely isolated from the common outlet. Moreover, as will now be described in detail, a mechanical interlock mechanism prevents more than one of the valves from being turned on at any time.

As shown in FIG. 3, the vaporizer selector valves 28 are mounted in a rectangular housing 64 beneath which the vaporizers 54, 56 and 60 are mounted. At the lower edge of the front face of the housing 64, three control levers 66, 68 and 70 are mounted for rotation about a common horizontal axis. As illustrated by the positions of levers 68 and 70, a control lever lowered to the off position partially covers its vaporizer and discourages access to the control knob 72. In addition, the levers 66 and 70 each have a pin 74, 76 depending from the lever to engage a corresponding slot in the vaporizer control knob when in the off position. In the on position, as shown by lever 66, the lever is raised through approximately ninety degrees, and the legend "VAPORIZER IN CIRCUIT" is exposed on the underside of the lever.

As best shown in FIG. 9, the levers 66, 68 and 70 are mechanically coupled by a cable interlock mechanism including one long cable 80 between the outer levers 66 and 70, and two shorter cables 81 and 82 between levers 66 and 68, and 68 and 70, respectively. The cables pass through guides 84. In addition, plastic pins 85 (best shown in FIG. 4) act as cable separators and guides. As also shown in FIG. 4, the guides 84 may be mounted for sliding movement generally perpendicular to the cable, and may be spring biased to remove slack from the tightened cables without over-tensioning them. Each of the levers 66, 68 and 70 has a pivot bushing, indicated by suffix a, about which it rotates, and a crank arm b extending from the bushing at approximately ninety degrees to the lever itself. The cable ends are secured in blocks c at the ends of the crank arms. In FIG. 9, lever 66 is in the on position, and it will be noted that its two cables 80 and 81 are fully tightened. Further, the two tight cables render it impossible to raise either of the other levers 68 or 70 without first lowering lever 66. As will shortly be appreciated, an attempt to raise one of the levers still in the off position has the effect of automatically returning the "on" lever to the off position.

FIG. 8 shows the detailed construction of an isolation valve and control lever assembly. In addition to the items already mentioned, the assembly includes a forked valve cam 86, whch is secured to a valve actuating shaft 44a by means of a valve pivot 88 and retaining screw 90 (FIG. 7). A torsion spring 92 has one end secured to the housing 64 and the other to a pin 94 on the valve cam 86, exerting a clockwise force on the valve cam as viewed in FIGS. 5, 6 and 8. A camming roller 70d mounted on the crank arm 70b engages the forked valve cam 86 to actuate the valve, as best shown in FIGS. 5 and 6.

In the off position shown in FIG. 5 the roller 70d engages a detent surface 86a in the valve cam 86, which is in a horizontal position. When the lever 70 is raised, the roller 70d at first moves easily along the forked valve cam 86, once the resistance of the detent is overcome. Then, as the valve cam 86 and crank arm 70b come into alignment a maximum actuating force must be applied to the lever to overcome the force of the spring 92. After this maximum point, the lever again enjoys increasing mechanical advantage, and less actuating force is required as the roller 70d moves back toward the detent surface 86a.

In the on position, shown in FIG. 6, the angle between the crank arm 70b and the valve cam 86 is slightly less then ninety degrees, and the clockwise force of the spring 92, together with the action of the detent surface 86b, tends to hold the lever in the on position. However, only a relatively small counterclockwise force on the lever 70 or crank arm 70b releases the mechanism from its detent and the lever will return to the off position solely under action of the spring 92.

It will be appreciated from the foregoing that the present invention represents a significant advance in the field of gas anesthesia machines. In particular, it provides a vaporizer subsystem for selecting one of a plurality of direct reading or universal vaporizers, while at the same time completely isolating non-selected vaporizers and providing a visual indication of which vaporizer is connected to the diluent flow. It will also be appreciated that, although a specific embodiment of the invention has been described in detail for purposes of illustration, various modifications may be made without departing from the spirit and scope of the invention. Accordingly, the invention is not to be limited except as by the appended claims.

I claim:

1. A vaporizer subsystem for use with a gas anesthesia machine providing a diluent flow of oxygen and anesthesia gas for selective diversion through one of a plurality of direct reading vaporizers, and providing an independent oxygen flow for selective diversion through at least one universal type vaporizer, said vaporizer subsystem comprising:

at least three isolation valves, operable independently of controls on the vaporizers, and each movable between an on position in which gas flow is diverted through a corresponding vaporizer and an off position in which the corresponding vaporizer is isolated; and interlock means for preventing more than one of said isolation valves from being switched to the one position at any particular time, wherein only a selected one of the vaporizers, whether of the direct-reading or the universal type, may be coupled to the anesthesia system at any time, and wherein said interlock means functions automatically to move a previously selected isolation value from its on position to its off position by selecting and actuating a different one of said isolation valves.

2. A vaporizer subsystem as set forth in claim 1, wherein:

said subsystem includes a plurality of valve control levers, one for each of said valves, and means for coupling each of said control levers to said corresponding valves; and said interlock means includes mechanical means for limiting movement of said control levers.

3. A vaporizer subsystem as set forth in claim 2, wherein:

said mechanical means includes a plurality of cables connecting said control levers and a plurality of guides over which said cables pass;

there is a separate one of said cables connecting every unique pair of said control levers; and each of said cables is of such length as to become taut on movement to the on position of one of said control levers connected to said cable, thereby preventing both control levers connected to the same cable from being in the on position at the same time;

whereby movement of a selected one of said control levers to the on position tightens the ones of said cables connected to said selected one of said control levers and prevents more than one control lever from movement to the on position.

4. A vaporizer subsystem as set forth in claim 2, wherein:

each of said control levers operating an isolation valve for a direct-reading vaporizer includes means for preventing the lever from returning to the off position unless the direct-reading vaporizer has its controls set to an off position.

5. A vaporizer subsystem as set forth in claim 2, wherein:

said means for coupling each of said control levers to said corresponding valves includes a torsion spring acting on the valve to bias it into an off position except when said control lever is fully in the on position.

6. A vaporizer subsystem for use with a gas anesthesia machine providing a diluent flow of oxygen and anesthesia gas, said vaporizer subsystem comprising:

at least two direct reading vaporizers through which the diluent flow may be selectively diverted;

at least one universal type vaporizer through which an independent flow of oxygen may be passed;

at least two isolation valves operable independently of controls on said vaporizers, and connected in series to the diluent flow, each movable between an on position in which the diluent flow is diverted through one of said direct reading vaporizers and an off position in which the corresponding vaporizer is bypassed;

at least one additional isolation valve connected in series with the independent oxygen flow and also movable independently of vaporizer controls between an on position in which the independent oxygen flow is diverted through said universal type vaporizer and an off position in which the vaporizer is bypassed;

a plurality of valve control levers, one for each of said isolation valves, including said additional one, said control levers also being movable between on and off positions;

means for coupling said control levers to said respective isolation valves; and interlock means for limiting movement of said control levers by preventing more than one of said control levers from being in the on position at the same time, and for automatically returning a previously selected one of said control levers to the off position upon movement of a different one of said control levers toward the on position.

7. A vaporizer subsystem as set forth in claim 6, wherein:

each of said control levers includes a pivot mounting, an operating handle and a crank arm with a cam follower mounted thereon;

said means for coupling includes a fork-like cam mounted for rotation to actuate said isolation valve;

said cam follower is engaged with said fork-like cam and, upon rotation of said crank arm, imparts rotation to said valve to move it to the on position; and said means for coupling also include a torsion spring acting to urge each valve to its off position, except when said control lever is in the on position, when said torsion spring acts through said cam and cam follower to hold control lever to the on position.

8. A vaporizer subsystem as set forth in claim 7, wherein said fork-like cam includes a detent for holding said control lever in both the on and off positions.

9. A vaporizer subsystem as set forth in claim 7, wherein:

said interlock means include a separate cable connecting each unique pair of said crank arms;

each of said separate cables is long enough to permit only one of the crank arms to which it is connected to be moved to the on position.

10. A vaporizer subsystem as set forth in claim 6, 7, 8 or 9, wherein said operating handles are shaped to partly cover corresponding vaporizers when in the off position, and to provide a clear visual indication of which vaporizer is connected.

11. A vaporizer subsystem as set forth in claim 10, wherein, if a first selected valve is in the on position, movement of a second one of said control levers toward the on position moves the first of said control levers out of the on position and allows it to return to the off position under action of said torsional spring coupled to said first selected valve.

* * * * *